(12) United States Patent
Datla et al.

(10) Patent No.: US 11,629,309 B2
(45) Date of Patent: Apr. 18, 2023

(54) SOLVENT FREE PROCESS FOR EXTRACTION OF CHOLESTEROL FROM MILK FAT

(71) Applicant: FERMENTA BIOTECH LIMITED, Thane (IN)

(72) Inventors: Anupama Datla, Mumbai (IN); Prashant Nagre, Thane West (IN); Jagdish Tamore, Thane West (IN); Sreenath Trivikram, Dombivili (IN); Amol Shirsath, Ambernath (IN)

(73) Assignee: FERMENTA BIOTECH LIMITED, Thane (IN)

( * ) Notice: Subject to any disclaimer, the term of this patent is extended or adjusted under 35 U.S.C. 154(b) by 79 days.

(21) Appl. No.: 16/634,812

(22) PCT Filed: Sep. 12, 2018

(86) PCT No.: PCT/IN2018/050590
§ 371 (c)(1),
(2) Date: Jan. 28, 2020

(87) PCT Pub. No.: WO2019/053742
PCT Pub. Date: Mar. 21, 2019

(65) Prior Publication Data
US 2020/0377818 A1    Dec. 3, 2020

(30) Foreign Application Priority Data

Sep. 14, 2017    (IN) .............................. 201721032630

(51) Int. Cl.
*C11B 3/00* (2006.01)
*A61K 31/59* (2006.01)
*A61K 31/593* (2006.01)
*C07J 9/00* (2006.01)

(52) U.S. Cl.
CPC ............ *C11B 3/001* (2013.01); *A61K 31/593* (2013.01); *C07J 9/00* (2013.01)

(58) Field of Classification Search
CPC ....... A61K 31/575; A61K 31/593; C07J 9/00; C11B 3/001; C11B 3/10; C11B 3/12
USPC .......................................... 514/784
See application file for complete search history.

(56) References Cited

U.S. PATENT DOCUMENTS

| 4,148,810 A | 4/1979 | Struve |
| 5,326,579 A | 7/1994 | Richardson et al. |
| 6,129,945 A | 10/2000 | Awad et al. |
| 2010/0136166 A1 | 6/2010 | Ye et al. |

FOREIGN PATENT DOCUMENTS

| EP | 0 318 326 A2 | 5/1989 |
| WO | 00/64921 A2 | 11/2000 |
| WO | 2016/096988 A1 | 6/2016 |

OTHER PUBLICATIONS

International Search Report dated Nov. 22, 2018 in connection with International Application No. PCT/IN2018/050590.

*Primary Examiner* — Sikarl A Witherspoon
(74) *Attorney, Agent, or Firm* — Kramer & Amado, P.C.

(57) ABSTRACT

The present invention discloses solvent free process for extracting cholesterol free of impurities from milk fat. The so isolated cholesterol is useful for the further preparation of vitamin D3. The present invention further provides pharmaceutical grade cholesterol from milk fat of high purity.

13 Claims, 1 Drawing Sheet

SOLVENT FREE PROCESS FOR EXTRACTION OF CHOLESTEROL FROM MILK FAT

FIELD OF INVENTION

The present invention relates to solvent free process for extracting cholesterol free of impurities from milk fat. The so isolated cholesterol is useful for the further preparation of vitamin D3. The present invention further provides pharmaceutical grade cholesterol from milk fat of high purity.

BACKGROUND OF THE INVENTION

Cholesterol, having IUPAC name (3β)-cholest-5-en-3-ol and which systematic name is 2,15-dimethyl-14-(1,5-dimethylhexyl)tetracyclo[8.7.0.02'7.011'15]heptacos-7-en-5-ol is a principal lipid sterol of all higher animals, distributed in body tissues, especially the brain and spinal cord. It can be found in large concentrations within the liver, spinal cord, and brain. Cholesterol is an important component of the membranes of cells, providing stability and is the major precursor for the biosynthesis of steroid hormones, bile and vitamin D.

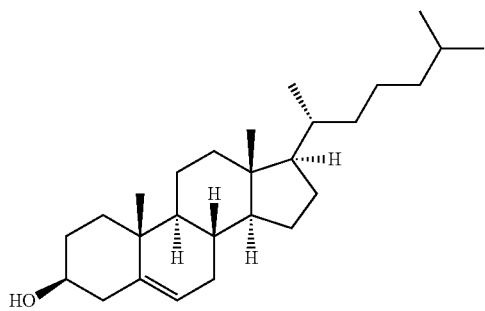

Cholesterol can be found in egg yolk, organ meat, shrimp, squid, beef, pork, poultry, fish, wool grease, full-fat dairy products, butter, hard margarines, lard, coconut oil, ghee (clarified butter), vegetable ghee, palm oil. These sources usually contain cholesterol in its free form as well as in the esterified form.

The most important source of cholesterol is lanolin, which is obtained from the wool of sheep. Raw wool contains three main impurities viz. wool grease, suint and dirt which make up to 30-40% of the fleece weight. The grease content of crossbred wool is about 6%. The wool grease is a very complex mixture consisting of esters of various long-chain fatty acids with long-chain alcohols and sterols. Wool grease is typically wax and not fat since glycerol esters are absent. The major part of the fatty acid present in wool grease consists of sterols; such as cholesterol, lanosterol and dihydrolanosterol with smaller amounts of other sterol derivatives. The other fatty acids present include normal paraffin series of C10 to C26, an iso-acid series from C10 to C28 even carbon atoms, an anteiso-acid series, with a terminal isobutyl group, with odd numbers of carbons from C9 to C31, α-hydroxy normal and iso-acids, like [R—CH(OH)—COOH] with even carbon numbers from about C12 to C32, n-alcohols from C18 to C30, Iso-alcohols from C18 to C26, anteiso-alcohols from C17 to C27 and 1,2 diols. The composition of fatty acids in wool grease is of complex nature given the different acids and alcohols present which can form varied esters.

To obtain cholesterol of pharmaceutical grade from wool grease is therefore limiting and demands for alternative sources for extraction of cholesterol which is cost-effective and industrially scalable.

One such source which is preferred in the art are dairy products selected form raw milk, pasteurized milk, raw cream, pasteurized cream, butter oil or anhydrous fat and such like which have large levels of cholesterol. The content of cholesterol in milk fat can vary, typically contains 2-5 gms total cholesterol per 100 grams. Further essentially all of the cholesterol in milk fat is present as free cholesterol with only traces of cholesterol present as an ester.

Many techniques are employed to extract cholesterol from milk fat such as steam stripping, supercritical fluid extraction (SFE) using carbon dioxide, specific enzymatic cholesterol reductase or adsorption using cyclodextrins. These processes are lengthy, cumbersome and expensive.

U.S. Pat. No. 5,326,579 disclose a process for the removal of cholesterol from a processed or un-processed dairy product using saponin as adsorbent at a temperature in the range of 35-80° C. and separating the insoluble cholesterol: saponin/diatomaceous earth by filtration or centrifugation. However, 3-β-Cholesterol esters present in the milk fat are found to not complex with saponin. The process described in US'579 does not isolate cholesterol in esterified form.

U.S. Pat. No. 6,129,945 disclose a process for removing free fatty acids (FFA) and preferably cholesterol from liquid anhydrous animal fats. The process uses a dilute solution of alkali metal base to form a salt of the FFA and then an alkali metal salt to precipitate the FFA from the animal fat. Preferably, a cyclo dextrin is used in the process to remove cholesterol. The process described in US'945 includes first saponification followed by separation of FFA (cholesterol) using beta-cyclo dextrin. The process described in US'945 is based on relatively long reaction time process at low temperature, requires controlled use of the amount of base for saponification which otherwise is detrimental to the yield due to the losses of neutral fat by saponification.

EP0318326 relates to a process of removing sterols from edible fat, specifically milk fat using a fixed and pulsed carbon column filled with adsorbents selected from carbon impregnated with a metal salt including zinc sulphate, zinc nitrate, zinc chloride, calcium chloride, manganese nitrate, manganese sulphate, manganese chloride; carbon impregnated with water soluble or alcohol soluble organic compounds selected from amides and nucleotides; porous glass, ceramic or plastics; aluminas, silicas, zeolites and magnesia which have/been impregnated with mineral salts and/or selected amides and nucleotides.

WO2016096988 describe the process for extraction of cholesterol from milk fat which includes saponification which is carried out preferably in a solvent or a mixture of solvent (for example alcohol/water mixture) followed by extraction with at least one non-water miscible solvent at elevated temperature. The process of WO'988 is liquid extraction of cholesterol at elevated temperature and the yields and purity are low.

In light of the commercial value of pharmaceutical grade cholesterol, which also acts as a precursor for production of vitamin D3, there exists a need in the art to provide cost effective and improved process for extraction of cholesterol from milk fat in high yield and purity. This remains the objective of the invention.

SUMMARY OF THE INVENTION

The objectives of the present invention are met by providing cost effective, solvent free process for extraction of cholesterol from milk fat wherein the cholesterol obtained is substantially free of impurities and can be used in the preparation of vitamin D3.

Accordingly, the solvent free process for extraction of cholesterol of high purity from milk fat characterized by the process steps comprising;
  i. heating unsaponified milk fat with anhydrous calcium chloride in molar ratio ranging from 1:1 to 1:12 to obtain $CaCl_2$-cholesterol adduct; and
  ii. separating cholesterol from the adduct by refluxing in the solvent followed by re-crystallization to yield pure cholesterol.

In an aspect, the present invention provides pharmaceutical grade cholesterol of milk fat characterized by HPLC purity in the range of 95-98%.

In another aspect, the present invention provides a process for production of vitamin D3 from pure cholesterol of milk fat obtained by the present invention. Accordingly, cholesterol is converted to 7-dehydrocholesterol (7-DHC; pro-vitamin D3) as per International Patent Publication No. WO 2015/170341, filed by the present Applicant, and converting 7-DHC to vitamin D3 by irradiation.

DETAILED DESCRIPTION OF THE INVENTION

Figure 1:
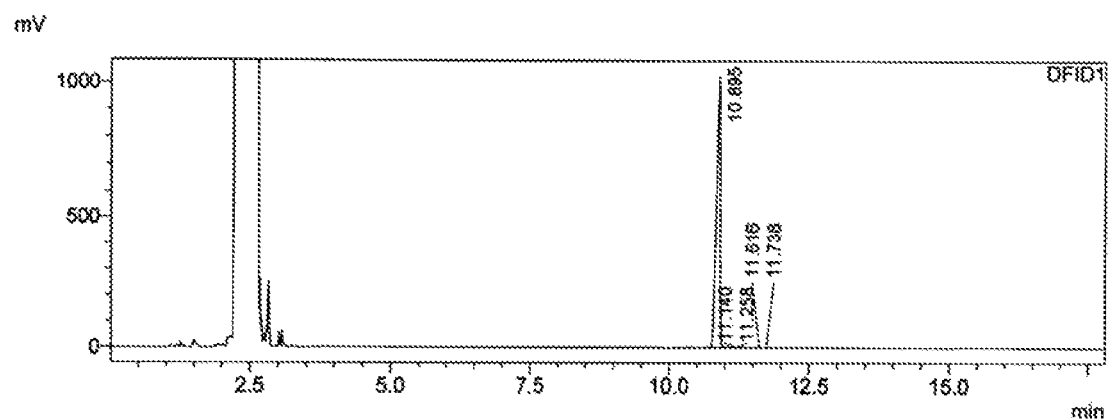
FIG. 1 depicts the chromatogram of Standard (STD) cholesterol.
Figure 2:
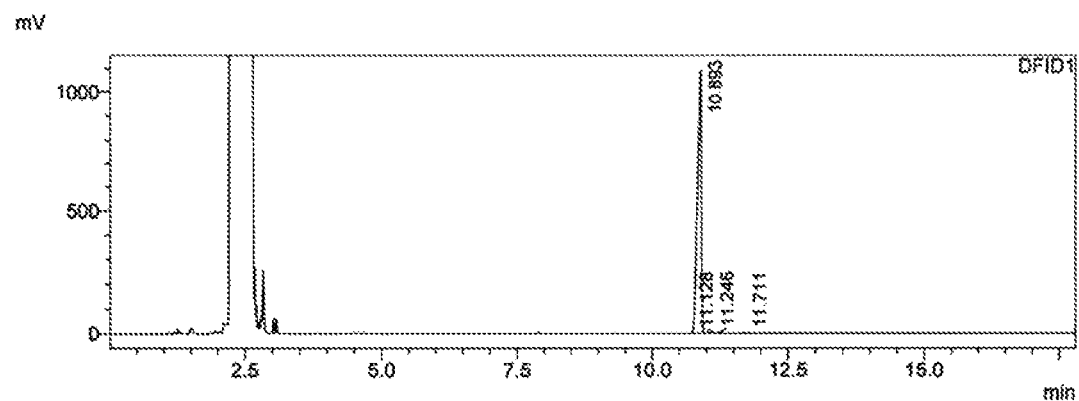
FIG. 2 depicts the chromatogram of cholesterol obtained by the present process.

The present invention relates to solvent free process for extraction of cholesterol of high purity from milk fat. The present process avoids the contact of milk fat with potentially harmful solvents in the initial stages that can affect the functionality, flavour or other properties of the milk fat. Further, there is no saponification thereby preventing the use of base, which may lead to losses of the neutral fat resulting in low yields of the desired product. The isolated milk fat free of cholesterol is washed with water to remove traces of inorganic impurities. The residual Milk fat free of cholesterol can be used by the milk industry for their own applications.

In an embodiment, the present invention relates to cost effective, solvent free process for extraction of cholesterol of high purity from milk fat characterized by the process steps which comprises;
  i. heating un-saponified milk fat with anhydrous calcium chloride in the ratio ranging between about 1:2 to about 1:20 to obtain $CaCl_2$-cholesterol adduct; and
  ii. separating cholesterol from the adduct by refluxing in the solvent followed by re-crystallization to yield pure cholesterol.

The milk fat of the present invention includes skim milk such as fluid skim milk, ultra-filtered skim milk, condensed skim milk and various derivatives of skim milk, whey products such as reconstituted fluid whey, whey powder, whey protein isolates, whole milk, reduced fat, reconstituted non-fat dry milk and the like that contribute significant amounts of cholesterol in these foods. The content of cholesterol typically ranges from 2-5 gms per gm of the milk fat.

Accordingly, the process comprises heating the sterol containing un-saponified milk fat with anhydrous calcium chloride in molar ratio ranging between about 1:2 to about 1:20, in solvent free medium, to obtain addition product of free cholesterol. The heating is performed at temperature in the range of 40–90° C., preferably 40-80° C., most preferably 75-85° C. for a period of 2-10 hours.

The reaction mass is then cooled to 40-50° C. and maintained at same temperature for 10-36 hours and filtered. The cholesterol adduct is suspended in organic solvent and refluxed for 1-10 hours, preferably 1-5 hours, more preferably 2-4 hours. The reaction mass is cooled to 0-50° C., preferably at 15-45° C., more preferably at 20-30° C., stirred at same temperature for about 2-3 hours, filtered, washed further with organic solvent and dried under vacuum to obtain cholesterol.

The isolated crude cholesterol is further purified by crystallization in solvent selected from lower alcohols such as methanol, ethanol, n-propanol, IPA, n-butanol, isobutanol or tert-butanol, preferably methanol or ketones selected from acetone, 2-Butanone, methyl isobutyl ketone, preferably acetone.

The residual milk fat free of cholesterol obtained after filtration of cholesterol-calcium chloride adduct satisfies the quality standard required by the Milk industry and can be used by Milk industry for their own applications.

In an embodiment, the cholesterol obtained by the present process is substantially free of impurities and is characterized by HPLC purity in the range of 95-99% as depicted in the comparative tables 1 and 2 below. The pharmaceutical grade cholesterol can be used as precursor for further preparation of vitamin D3.

TABLE 1

HPLC data of STD cholesterol (w.r.t FIG. 1)

| Peak No. | Retention time | Area | Height | Area % |
|---|---|---|---|---|
| 1. | 10.895 | 4714241 | 1020260 | 99.335 |
| 2. | 11.140 | 14800 | 4917 | 0.312 |
| 3. | 11.258 | 12567 | 4208 | 0.265 |
| 4. | 11.616 | 2640 | 739 | 0.056 |
| 5. | 11.738 | 1544 | 400 | 0.033 |
| Total | | 4745792 | 1030524 | 100.000 |

TABLE 2

HPLC data of cholesterol obtained by the present process (w.r.t FIG. 1)

| Peak No. | Retention time | Area | Height | Area % |
|---|---|---|---|---|
| 1. | 10.893 | 5311138 | 1083092 | 99.337 |
| 2. | 11.128 | 4877 | 1305 | 0.091 |
| 3. | 11.246 | 16260 | 5626 | 0.304 |
| 4. | 11.711 | 14315 | 2456 | 0.268 |
| Total | | 5346590 | 1092479 | 100.000 |

In another embodiment, the process for preparation of vitamin D3 from pharmaceutical grade cholesterol obtained from milk fat of the present invention which comprises (a) converting cholesterol to 7-dehydrocholesterol (7-DHC; pro-vitamin D3) as per International Patent Publication No. WO 2015/170341, filed by the present Applicant, and (ii) converting 7-DHC to vitamin D3 by irradiation.

In the advantageous embodiment of the present invention, the milk fat used for extraction of cholesterol is not exposed to solvents in the initial stages due to which the functionality, flavour or other properties of the milk fat are not disturbed; there is no saponification thereby preventing the use of base, which may lead to losses of the neutral fat resulting in low yields of the desired product; the residual milk fat free of cholesterol of good quality can be used by the Milk Industry for further applications according to their requirement. The cholesterol obtained by the present process is of pharmaceutical grade and can be used as precursor for further preparation of vitamin D3. The process is simple and industrially feasible with minimum work up steps.

The example herein is provided to illustrate particular aspect of the disclosure and do not limit the scope of the present invention.

Example 1: Cholesterol from Milk Fat

Milk fat (100 gms) and anhydrous calcium chloride (8.5 gms) were heated at 80° C. for 2-4 hours. The reaction mass was cooled to 45° C. and maintained at same temperature for 15 hours. The reaction mass was filtered at 45° C., and the solid residue of cholesterol-adduct was suspended in methanol (100 ml). The reaction mass was refluxed for 4-6 hours, cooled to 25-30° C., stirred at same temperature for 2-3 hours, filtered and washed with methanol (10 ml) to obtain crude cholesterol. The crude cholesterol was recrystallized by dissolving in methanol (100 ml), filtered, washed with 20-50 ml of cold Methanol, dried under vacuum at 45° C. to obtain pure cholesterol.

Yield: 35 gms

HPLC Purity: 96-99%.

It is to be understood that the above description is intended to be illustrative and not restrictive. Many embodiments will be apparent to a person skilled in the art upon reviewing the description. The scope of the invention should therefore, be determined not with reference to the above description, but instead should be determined with reference to the appended claims, along with the full scope of equivalents to which such claims are entitled.

We claim:

1. A process for extraction of cholesterol from milk fat, comprising:
   i. a solvent-free step of heating un-saponified milk fat with anhydrous calcium chloride to obtain a $CaCl_2$-cholesterol adduct; and
   ii. separating cholesterol from the $CaCl_2$-cholesterol adduct by refluxing the $CaCl_2$-cholesterol adduct in an organic solvent, followed by re-crystallization of cholesterol.

2. The process as claimed in claim 1, wherein the solvent-free step includes heating un-saponified milk fat and anhydrous calcium chloride in a molar ratio ranging from 1:1 to 1:12.

3. The process as claimed in claim 1, wherein the solvent-free step includes heating at a temperature ranging from 40° C. to 90° C.

4. The process as claimed in claim 3, wherein the solvent-free step includes heating at a temperature ranging from 75° C. to 85° C.

5. The process as claimed in claim 1, wherein the solvent in the step of separating cholesterol is selected from the group consisting of a lower alcohol, a ketone, and a mixture thereof.

6. The process as claimed in claim 1, wherein the solvent in the step of separating cholesterol is selected from the group consisting of methanol, ethanol, n-propanol, isopropyl alcohol, n-butanol, isobutanol, tert-butanol, and a mixture thereof.

7. The process as claimed in claim 1, wherein the solvent in the step of separating cholesterol is selected from the group consisting of acetone, 2-Butanone, methyl isobutyl ketone, and a mixture thereof.

8. The process as claimed in claim 1, wherein the step of separating cholesterol produces cholesterol having a purity in ranging from 95% to 98%, based on HPLC.

9. A process for synthesis of vitamin D3, comprising:
   extracting cholesterol from milk fat by the process of claim 1;
   converting cholesterol to 7-dehydrocholesterol (7-DHC); and
   converting 7-DHC to vitamin D3 by irradiation.

10. A process for synthesis of vitamin D3, comprising:
    extracting cholesterol from milk fat by:
       heating un-saponified milk fat with anhydrous calcium chloride in a molar ratio ranging from 1:1 to 1:12 to obtain a $CaCl_2$-cholesterol adduct; and
       separating cholesterol from the $CaCl_2$-cholesterol adduct by refluxing the $CaCl_2$-cholesterol adduct in a solvent;
    converting the separated cholesterol to 7-dehydrocholesterol (7-DHC); and
    converting 7-DHC to vitamin D3 by irradiation.

11. The process as claimed in claim 10, wherein the heating step includes heating un-saponified milk fat and anhydrous calcium chloride.

12. The process as claimed in claim 10, wherein the step of heating un-saponified milk fat is a solvent-free step, and wherein the solvent-free step includes heating at a temperature ranging from 40° C. to 90° C.

13. The process as claimed in claim 10, wherein the solvent in the step of separating cholesterol is selected from the group consisting of:
    a lower alcohol selected from the group consisting of methanol, ethanol, n-propanol, isopropyl alcohol, n-butanol, isobutanol, tert-butanol, and a mixture thereof; and
    a ketone selected from the group consisting of acetone, 2-Butanone, methyl isobutyl ketone, and a mixture thereof.

* * * * *